US00PP18013P2

(12) United States Plant Patent
Strode

(10) Patent No.: US PP18,013 P2
(45) Date of Patent: Sep. 11, 2007

(54) ***SYNGONIUM* PLANT NAMED 'NEON ROBUSTA'**

(50) Latin Name: *Syngonium podophyllum*
Varietal Denomination: Neon Robusta

(75) Inventor: Randall E. Strode, Longwood, FL (US)

(73) Assignee: Agri-Starts, Inc., Apopka, FL (US)

( * ) Notice: Subject to any disclaimer, the term of this patent is extended or adjusted under 35 U.S.C. 154(b) by 0 days.

(21) Appl. No.: 11/351,849

(22) Filed: Feb. 10, 2006

(51) Int. Cl.
*A01H 5/00* (2006.01)

(52) U.S. Cl. ..... Plt./374
(58) Field of Classification Search ..... Plt./374
See application file for complete search history.

*Primary Examiner*—Kent Bell
*Assistant Examiner*—Louanne Krawczewicz Myers
(74) *Attorney, Agent, or Firm*—C. A. Whealy

(57) ABSTRACT

A new and distinct cultivar of *Syngonium* plant named 'Neon Robusta', characterized by its upright and symmetrical plant shape; freely branching growth habit; dense and bushy plant form; and iridescent pink-colored upper leaf surfaces.

2 Drawing Sheets

Botanical designation: *Syngonium podophyllum.*
Cultivar denomination: 'Neon Robusta'.

BACKGROUND OF THE INVENTION

The present Invention relates to a new and distinct cultivar of *Syngonium* plant, botanically known as *Syngonium podophyllum* and hereinafter referred to by the name 'Neon Robusta'.

The new *Syngonium* is a naturally-occurring branch mutation of the *Syngonium podophyllum* cultivar Neon, not patented. The new *Syngonium* was discovered and selected by the Inventor on Jun. 6, 2003 in a controlled environment in Apopka, Fla. on a single plant of the cultivar of Neon.

Asexual propagation of the new cultivar by tissue culture since June, 2003, in a controlled environment in Apopka, Fla., has shown that the unique features of this new *Syngonium* are stable and reproduced true to type in successive generations.

SUMMARY OF THE INVENTION

The following traits have been repeatedly observed and are determined to be the unique characteristics of 'Neon Robusta'. These characteristics in combination distinguish 'Neon Robusta' as a new and distinct cultivar of *Snygonium:*

1. Upright and symmetrical plant shape.
2. Freely branching growth habit; dense and bushy plant form.
3. Iridescent pink-colored upper leaf surfaces.

In side-by-side comparisons conducted by the Inventor in Apopka, Fla., plants of the new *Syngonium* differed primarily from plants of the parent, the cultivar Neon, in leaf color as plants of the cultivar Neon had fainter pink-colored leaves.

Plants of the new *Syngonium* can be compared to plants of the cultivar Regina, not patented. In side-by-side comparisons conducted in Apopka, Fla., plants of the new *Syngonium* differed from plants of the *Syngonium* cultivar Regina in the following characteristics:

1. Plants of the new *Syngonium* are more compact than plants of the cultivar Regina.

2. Plants of the new *Syngonium* are more freely branching than plants of the cultivar Regina.
3. Upper leaf surfaces of plants of the new *Syngonium* are more intense pink in color than upper leaf surfaces of plants of the cultivar Regina.

BRIEF DESCRIPTION OF THE PHOTOGRAPHS

The accompanying colored photographs illustrate the overall appearance of the new *Syngonium,* showing the colors as true as it is reasonably possible to obtain in colored reproductions of this type. Colors in the photographs may differ slightly from the color values cited in the detailed botanical description which accurately describe the colors of the new *Syngonium.*

The photograph on the first sheet comprises a side perspective view of a typical plant of 'Neon Robusta' grown in a container.

The photograph at the top of the second sheet is a close-up view of the upper surface of a typical leaf of 'Neon Robusta'.

The photograph at the bottom of the second sheet is a close-up view of the lower surface of a typical leaf of 'Neon Robusta'.

DETAILED BOTANICAL DESCRIPTION

The cultivar Neon Robusta has not been observed under all possible environmental conditions. The phenotype may vary somewhat with variations in environment such as temperature and light intensity without, however, any variance in genotype. The following observations and measurements describe plants of the new *Syngonium* that were grown in 15-cm containers, in Sebring, Fla. in a polycarbonate-covered greenhouse with light levels about 5,000 foot-candles. During the production of the plants, day temperatures ranged from about 21° C. to about 33° C. and night temperatures ranged from about 10° C. to about 20° C. Plants used for the photographs and description were about four months from planting. Color references are made to The Royal Horticultural Society Colour Chart, 2001 Edition, except where general terms of ordinary dictionary significance are used.

Botanical classification: *Syngonium podophyllum* cultivar Neon Robusta.

Parentage: Naturally-occurring branch mutation of the *Syngonium podophyllum* cultivar Neon, not patented.

Propagation:

*Type.*—By tissue culture.

*Time to initiate roots, summer.*—About 10 days at 29° C.

*Time to initiate roots, winter.*—About 20 days at 20° C.

*Time to produce a rooted plant, summer.*—About 70 days at 29° C.

*Time to produce a rooted plant, winter.*—About 84 days at 20° C.

*Root description.*—Thick and fleshy with fine laterals; N199C to N199D in color; root tips, 160B to 160C; strong root system.

Plant description:

*Plant form.*—Upright and symmetrical plant form; rounded inverted triangle.

*Growth habit.*—Plant size appropriate for 10-cm to 20-cm containers.

*Growth habit.*—Plants are freely clumping; usually about eight branch stems develop per plant; dense and bushy plant form. Moderately vigorous growth habit.

*Plant height.*—About 18 cm.

*Plant width* (*spread*).—About 33 cm.

*Stem description.*—Length (from soil surface to junction of the last two unrolled leaves): About 3 cm. Diameter: About 7 mm. Internode length: About 1 cm. Texture: Smooth, glabrous. Strength: Sturdy, flexible; upright. Color, immature: between 145D and 147D. Color, mature: 147A to 147D depending on exposure to light.

*Foliage description.*—Arrangement: Alternate; simple. Length: About 11.1 cm. Width: About 7.6 cm. Shape: Ovate. Apex: Acuminate to cuspidate. Base: Sagittate. Margin: Entire; somewhat undulate. Aspect: Mostly flat; between primary veins, convex. Texture, upper and lower surfaces: Smooth, glabrous. Venation pattern: Pinnate. Color: Developing leaves, upper surface: 182B; towards the petiole, tinged with 182A; towards the margin, tinged with 147C to 147D; midrib, 182A to 182B. Developing leaves, lower surfaces: between 147C and 146C; midrib, 146C. Fully expanded leaves, upper surface: 182B to 182C; towards the petiole, tinged with 182B; towards the margin, tinged with 147C to 147D; midrib and lateral veins, 182B to 182C. Fully expanded leaves, lower surface: 147B; midrib, 147C; mid veins, 147C; lateral veins, 147B. Petiole: Length: About 15.6 cm. Diameter, distal: About 2 mm. Diameter, proximal: About 1.3 cm. Color: 147C to 147D. Wing length: About 3.9 cm. Wing diameter: About 8 mm. Wing color, outer surface: 147C to 147D streaked with 182C. Wing color, inner surface: 182A to 182B; along margin and midline, 147C to 147D.

Inflorescence description: Inflorescence development has not been observed on plants of the new *Syngonium.*

Disease/pest resistance: Plants of the new *Syngonium* have not been observed to be resistant to pathogens and pests common to *Syngonium.*

Temperature tolerance: Plants of the new *Syngonium* have been observed to be tolerant to temperatures ranging from about 10° C. to about 40° C.

It is claimed:

1. A new and distinct cultivar of *Syngonium* plant named 'Neon Robusta', as illustrated and described.

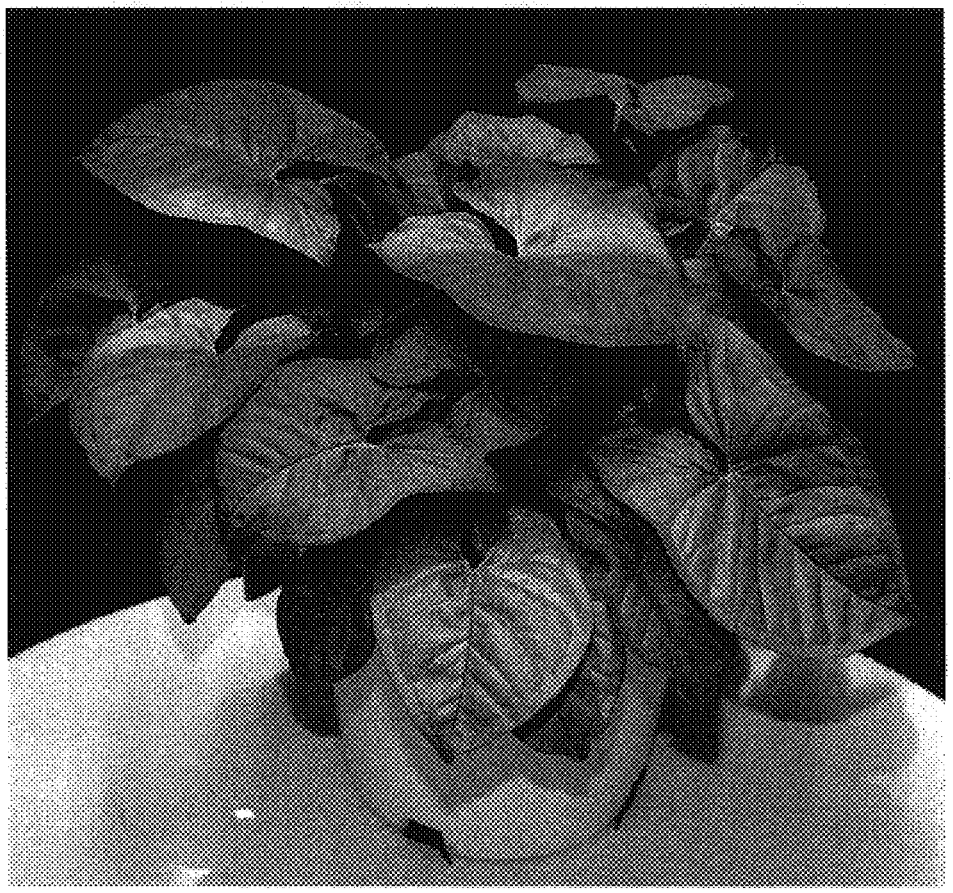

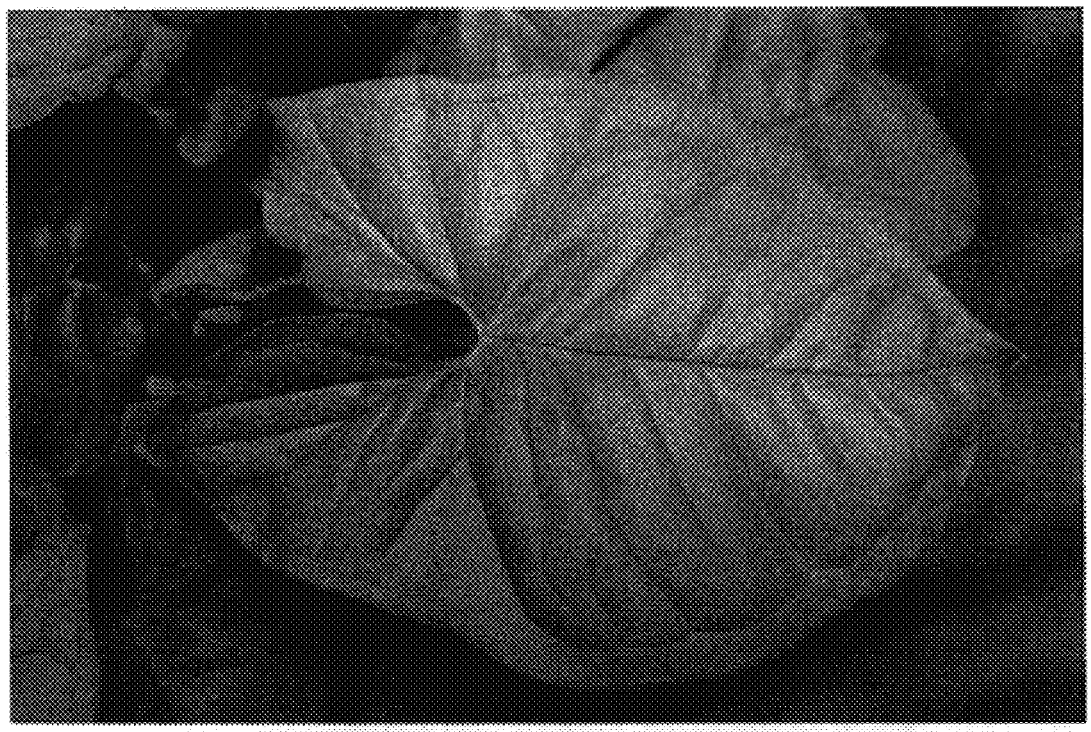
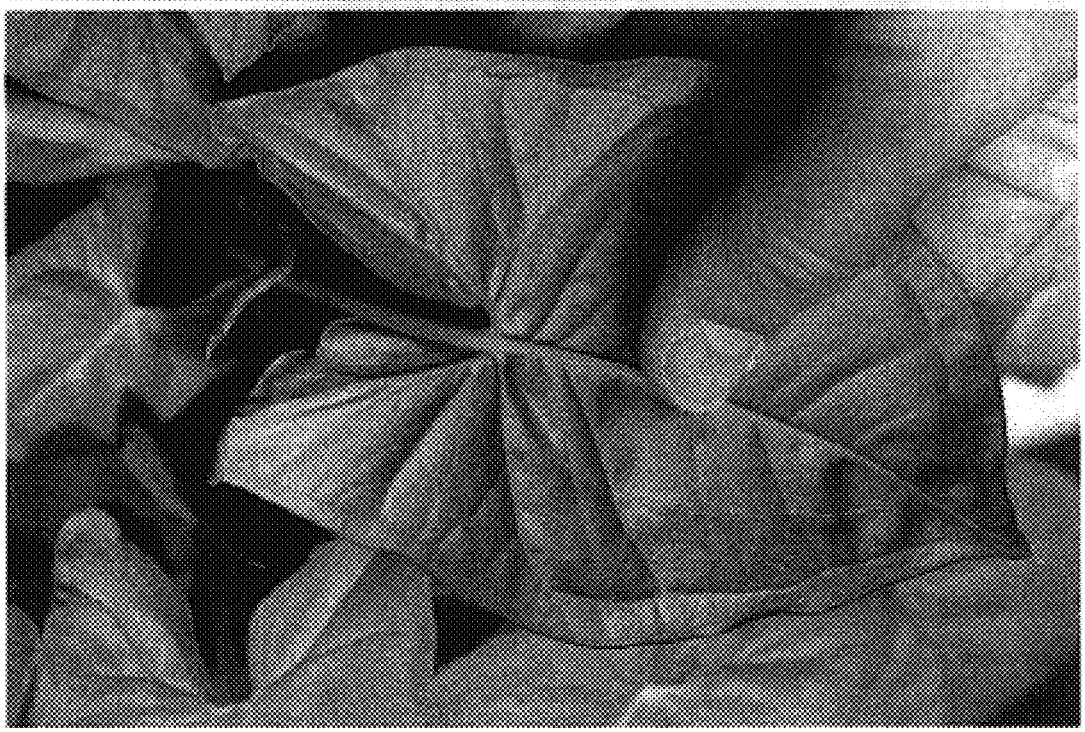

* * * * *